United States Patent [19]

Chaudhary et al.

[11] Patent Number: 5,614,503
[45] Date of Patent: Mar. 25, 1997

[54] AMPHIPATHIC NUCLEIC ACID TRANSPORTER

[75] Inventors: Nilabh Chaudhary; Krishna Jayaraman; Veeraiah Bodepudi; Michael E. Hogan, all of The Woodlands, Tex.

[73] Assignee: Aronex Pharmaceuticals, Inc., The Woodlands, Tex.

[21] Appl. No.: 467,114

[22] Filed: Jun. 6, 1995

Related U.S. Application Data

[63] Continuation of Ser. No. 303,554, Sep. 8, 1994, abandoned, which is a continuation of Ser. No. 152,544, Nov. 12, 1993, abandoned.
[51] Int. Cl.$^6$ .......................... A61K 9/127; A61K 48/00; C07J 9/00; C07C 261/00
[52] U.S. Cl. .......................... 514/44; 424/450; 536/23.1; 552/544; 562/555; 935/52; 935/54
[58] Field of Search .......................... 514/44; 536/23.1; 560/240; 435/172.1; 935/52, 54; 552/544; 562/555; 424/450

[56] References Cited

PUBLICATIONS

N Miller et al (1994) Parasitology Today 10: 92–97.
RA Stull et al (1995) Pharmaceutical Research 12: 465–483.
S Wu–Pong (1994) Pharmaceutical Technology 118: 102–114.
RW Wagner (1994) Nature 372: 333–335.
JP Behr et al (1989) Proc Natl Acad Sci USA 86:6982–6986.

*Primary Examiner*—Bruce R. Campell
*Attorney, Agent, or Firm*—C. Steven McDaniel; Conley, Rose & Tayon, P.C.

[57] ABSTRACT

A nucleic acid transporter to deliver a nucleic acids into cells, comprising a cationic compound having a cationic head group for binding the nucleic acid and a lipid tail for association with the membrane. A cationic compound usually is a polyamine or a short basic peptide. The lipid tail is usually selected from the group consisting of plant steroid, animal steroid, isoprenoid compound, aliphatic lipid, pore forming protein, pore forming peptides and fusogenic peptides. The cationic head and the lipid tail are linked through a carbamate linkage. When polyamine is used, it is preferably either spermidine or spermine and the nucleic acid can be any of a variety, including triplex forming oligonucleotides, antisense oligonucleotide, aptamers, ribozymes, plasmids and DNA for gene therapy. Also described is a method for treating individuals using the transporter linked to a therapeutic nucleic acid.

9 Claims, 3 Drawing Sheets

AMPHIPATHIC NUCLEIC ACID TRANSPORTER

This invention was supported in part by a grant from the United States Government through the National Institute of Health. The Government has certain rights in this invention.

This application is a continuation of application Ser. No. 08/303,554, filed Sep. 08, 1994, abandoned, which is a continuation of Ser. No. 08/152,544, filed Nov. 12, 1993, abandoned.

FIELD OF INVENTION

The present invention generally relates to a method of transporting nucleic acids into cells. More specifically, it relates to linking a polyamine or short basic peptide to a lipid compound for transporting nucleic acids into cells.

BACKGROUND OF THE INVENTION

It has been known that certain cationic lipids, e.g., DOTMA (Felgner, *Adv. Drug Delivery Rev.* 5:163, 1990), can improve the uptake kinetics of nucleic acids in some types of animal cells. Unfortunately, the commercially available preparations of cationic lipids are frequently cytotoxic at concentrations necessary for achieving cellular uptake. In addition, these compounds are not always effective for delivering material to different types of cell populations.

There are a number of commercially available cationic lipids purported to improve the cellular entry of nucleic acids. The prototype compound, DOTMA (Felgner), has been widely used for improving transfection efficiency of cells. This compound is the active ingredient of the commercially available liposomal preparation Lipofectin (Gibco-BRL). Gibco-BRL also markets Lipofectace and Lipofectamine for the same purpose. Boehringer Mannheim supplies DOTAP, and Promega markets Transfectam. Most of these preparations have stringent requirements for administration to cells (e.g., a requirement for a low serum medium, specificity of cell types, quality of nucleic acids) and many are cytotoxic. Gao and Huang (*Biochem. Biophys. Res. Comm.* 179:280, 1991) have described a cholesterol-containing cationic lipid that is used as a component of liposomes with the potential to enhance the cellular uptake of nucleic acids. However, the structure of the cationic group and the mode of usage of the compound are different from the compounds of the present invention. An amino-sterol, squalamine, isolated from shark tissues, has been shown to be a broad-spectrum antibiotic by Moore et al. (*Proc. Natl. Acad. Sci.* 90:1354, 1993). This compound is a cationic steroid in which an anionic bile salt intermediate is linked to spermidine. Moore et al. did not suggest any use of the compound in improving nucleic acid delivery into cells. We are not aware of other publications that describe compounds identical or similar to the ones in this disclosure.

There is a real need in the field of nucleic acid therapeutics to develop nonviral uptake enhancement reagents that are nontoxic and effective in a variety of cell types. The numerous commercial preparations are widely perceived to be ineffectual or of limited value for most aspects of nucleic acid delivery. The present invention addresses this problem by the synthesis of simple, relatively nontoxic cationic compounds that improve the cellular and nuclear delivery of nucleic acids.

SUMMARY OF THE INVENTION

An object of the present invention is to provide a transporter for moving nucleic acids into the cell and into the nucleus.

Another object of the present invention is to provide a transporter for moving triplex forming oligonucleotides into the cell and into the nucleus.

A further object of the present invention is the provision of a treatment method using therapeutic nucleic acids linked to a transporter.

Thus, in accomplishing the foregoing objects, there is provided in accordance with one aspect of the present invention a relatively non-toxic, amphipathic transporter for delivery of nucleic acids into cells, comprising a cationic compound having a cationic head group for binding the nucleic acid and a lipid tail for association with the membrane; said cationic compound being a polyamine or a short basic peptide; said lipid tail being selected from the group consisting of plant steroid, animal steroid, isoprenoid compound, aliphatic lipid, pore forming protein or peptide and fusogenic peptide; and wherein the cationic head is linked to the lipid tail through a carbamate linkage.

In the specific embodiments of the present invention, the cationic head group is a polyamine and selected from the group consisting of spermidine or spermine and the lipid tail is cholesterol.

In another embodiment, the transporter is linked to a therapeutic nucleic acid. This combined nucleic acid/transporter can be used to treat disease.

Other and further objects, features and advantages will be apparent in the following description of the presently preferred embodiments of the invention given for the purpose of disclosure when taken in conjunction with the accompanying drawings.

Figure 1:
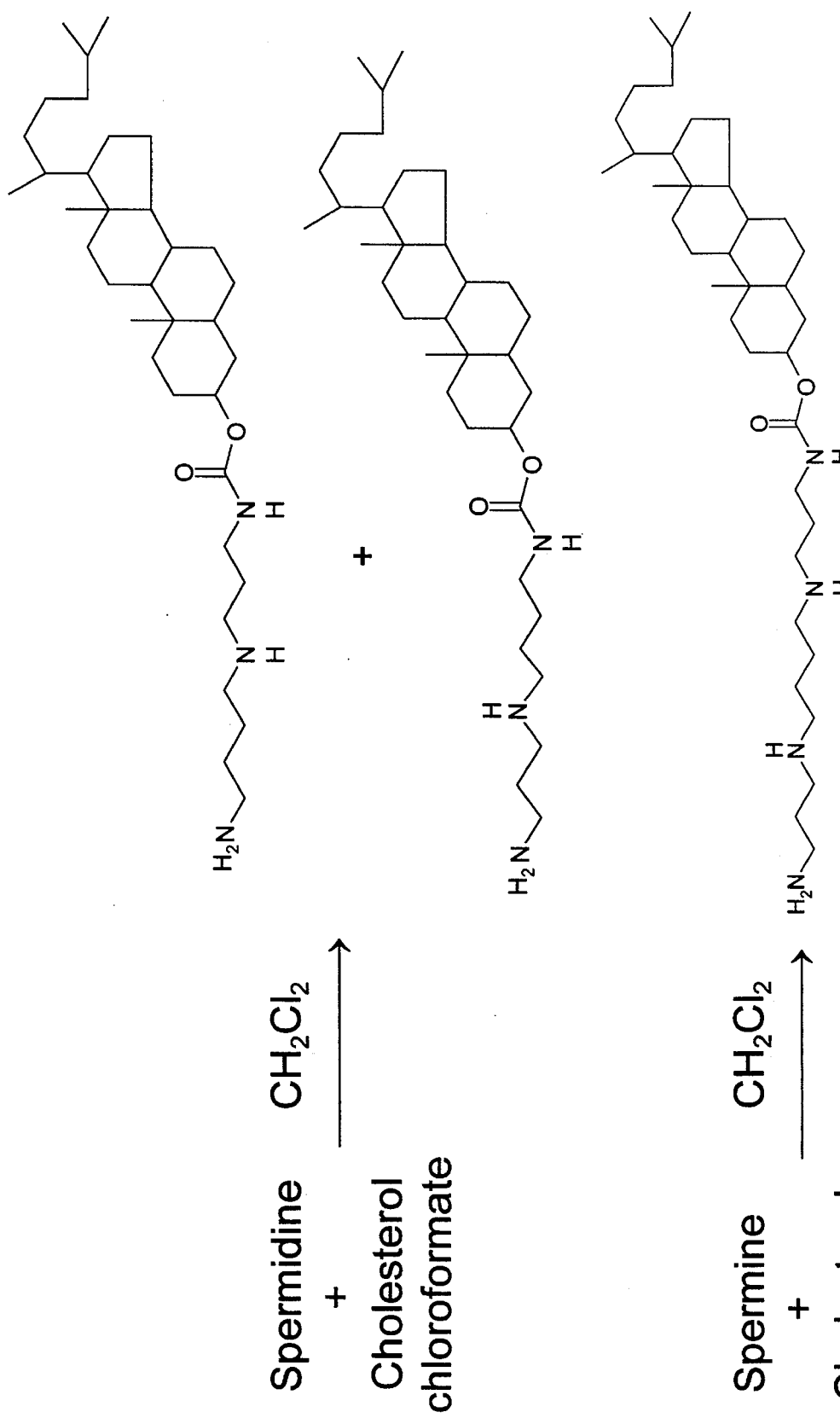
FIG. 1 is a schematic representation of a transporter showing a polyamine linked to a lipid through a carbamate linkage.

The drawings are not necessarily to scale. Certain features of the invention may be exaggerated in scale or shown in schematic form in the interest of clarity and conciseness.

DETAILED DESCRIPTION

It is readily apparent to one skilled in the art that various substitutions and modifications may be made to the invention disclosed herein without departing from the scope and spirit of the invention.

The term "synthetic oligonucleotides" as used herein is defined as molecules, comprising two or more deoxyribonucleotides or ribonucleotides, preferably more than ten. The exact size would depend on many factors, including the specificity and binding affinity.

The term "TFO" or "triplex forming oligonucleotide" as used herein refers to the synthetic oligonucleotides which are capable of forming a triplex by binding to the major groove of a duplex DNA structure.

As used herein, a "short basic peptide" includes a peptide of two or more amino acids containing the amino acids arginine and lysine that are prevalent in proteins that bind to nucleic acids.

The term "therapeutic nucleic acid" as used herein means any nucleic acid which can be used for the therapy of disease in humans or animals. This includes triplex forming oligonucleotides, antisense oligonucleotides, aptamers, ribozymes, plasmids and DNA for gene therapy. Once a therapeutic nucleic acid has been developed, the methods described in the present invention can be used to facilitate the introduction of the therapeutic nucleic acid into the cells. In this method the therapeutic nucleic acid is combined with the transporter. The therapeutic nucleic acid binds to the cationic head group. The combined therapeutic nucleic acid/transporter can then be delivered to the individual (human or animal) to be treated. Delivery can be any of the variety of techniques known to those skilled in the art. Examples of some of the techniques include oral, parental and direct injection.

The word "bound" when used in the context of a nucleic acid bound to the transporter refers to the association of the head group with the nucleic acids by electrostatic, hydrophobic, ionic or other non-covalent interaction. One skilled in the art will recognize that the specific binding which is most useful in the present invention will depend on the specific head group and nucleic acid which are combined.

One embodiment of the present invention is a non-toxic amphipathic transporter for delivery of nucleic acids into cells. The transporter is comprised of a cationic compound having a cationic head group for binding nucleic acids and a lipid tail for association with a membrane. The cationic compound is usually selected from a group consisting of polyamine or a short basic peptide. The lipid tail is usually selected from the group consisting of plant steroid, animal steroid, isoprenoid compound, aliphatic lipid, pore forming protein, pore forming peptide and a fusogenic peptide. In the transporter, the cationic head is linked to the lipid tail through a carbamate linkage.

Although the mechanism of action of the transporter is not known, it is expected that the most effective compounds have a cationic head group for binding to nucleic acids, and a lipid tail to associate with membranes. In addition, the components of the transporter should have minimal toxicity and be biodegradable.

In one embodiment the transporter has polyamines (spermine or spermidine) attached to cholesterol through a carbamate linkage (FIG. 1). The polyamines are ubiquitous in all animal cell types, and cholesterol is a component of cellular membranes.

One skilled in the art recognizes that other related amphipathic compounds can be used. In each case the transporter contains a cationic group attached to a membrane-interactive moiety. The two functional domains are essential for improving the transmembrane movement of the oligonucleotides. The cationic group can be any polyamine or short basic peptides. The hydrophobic group could be any naturally occurring lipid. For example, these can include animal or plant steroids, isoprenoid compounds such as farnesol, aliphatic lipids, pore forming proteins, pore forming peptides, and fusogenic peptides.

The following examples are offered by way of illustration and are not intended to limit the invention in any manner.

EXAMPLE 1

Synthesis of Polyamine-Cholesterol Conjugates

Cholesteryl chloroformate was added dropwise to a solution of spermidine or spermine in methylene chloride and N,N-diisopropyl ethylamine, and stirred at room temperature for 2 hours. The product was purified by chromatographic methods and characterized by standard physical and spectroscopic methods. The final preparation, a white solid (>95% purity) (FIG. 1), was solubilized and used in standard oligonucleotide uptake assays.

EXAMPLE 2

Cytotoxicity of Cationic Lipids

Cell proliferation was measured by the Cell Titer 96 Aqueous Non Radioactive Cell Proliferation Assay (Promega). The absorbance at 490 nm is directly proportional to the number of living cells. Vero cells were plated at an initial density of 500 cells/well. After 20 hours, cells were exposed to different concentrations of cationic lipid for 4 days. Data points in FIG. 2 are the average of replicates for each test concentration.

Figure 2:
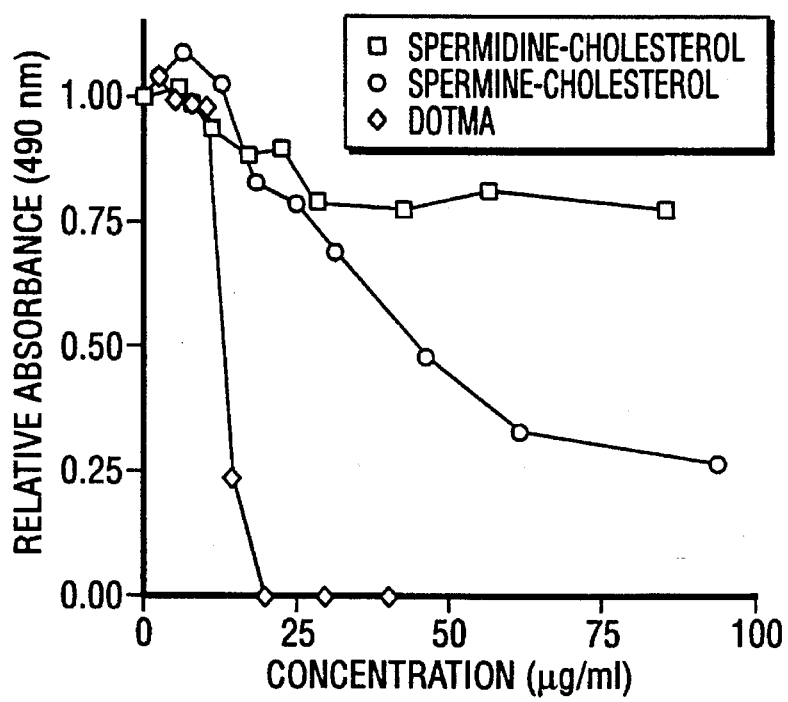
FIG. 2 shows the effect of cationic lipid compounds on the proliferation of Vero cells.

From FIG. 2 it can be seen that the novel cationic compounds are less toxic than DOTMA, as assessed by this highly sensitive cell proliferation assay. The polyamine-cholesterol derivatives are typically used in cell culture-based biological assays at concentrations ranging from 2 to 10 μg/ml, at effectively nontoxic levels.

EXAMPLE 3

Cellular Uptake Experiments

Vero cells were treated with 1 μM $^{35}$S-labeled oligonucleotide-propylamine coadministered with one of the 3 cationic lipids, as indicated, at about a 1:2 mass ratio. For Lipofectin only, the extracellular medium contained no serum, as suggested by the manufacturer. At various time points (0–24 h), the uptake of radiolabeled oligonucleotides was evaluated by scintillation counting, and intracellular concentration was calculated based on the known specific activity of the radiolabeled oligonucleotides.

In the standard assay, the 3' end-protected oligonucleotides (e.g., oligo-3'-propylamine; Zendegui et al., *Nuc. Acid Res.* 20:307, 1992) are premixed with the cationic compounds and added to cells. The optimal ratio of oligonucleotides to cationic group must be determined empirically. Usually, a ratio of 1:2 by mass results in enhanced cellular uptake. The internalized compounds can be traced using biological assays, or by attaching a radiolabel or a fluorophore to the nucleic acid.

Figure 3:
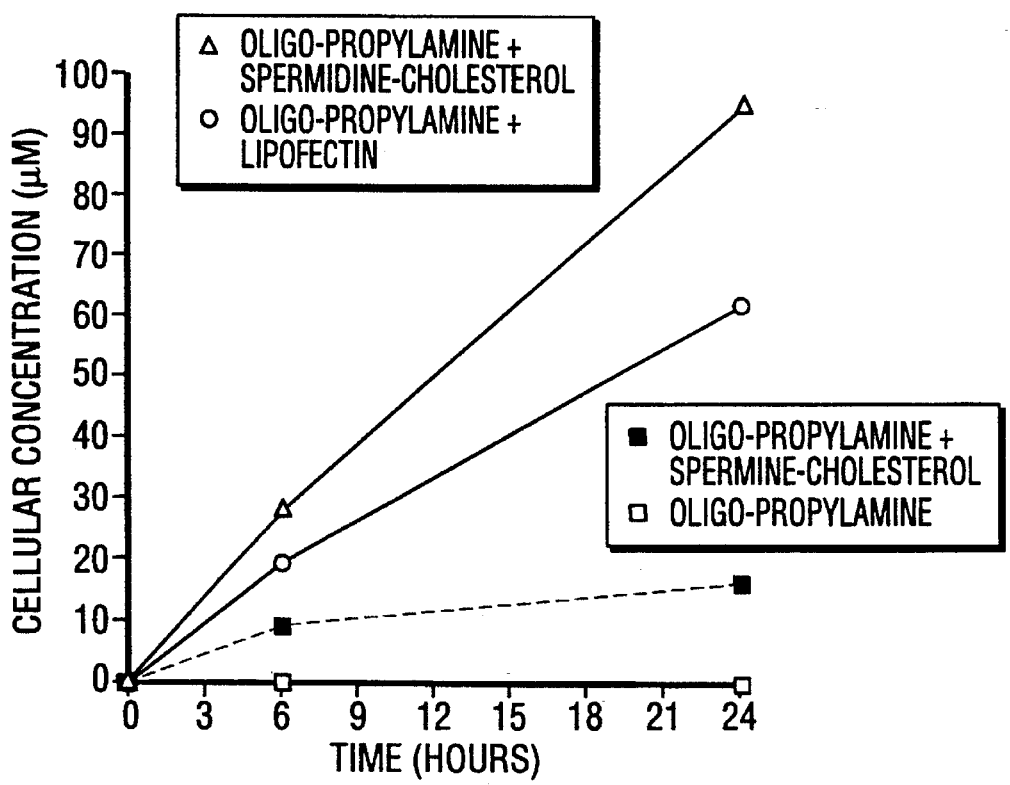
FIG. 3 shows the enhanced cellular uptake of oligonucleotides in the presence of cationic lipids.

Internalization of oligonucleotide-cationic lipid complex occurs rapidly, within 20–40 minutes, and fluorescence microscopy experiments suggest that a portion of the internalized oligonucleotides enter the nucleus. Using radiolabeled material, the uptake-enhancement effect is estimated to be up to 100 fold greater than if cells are treated with oligomers alone (FIG. 3). The improved uptake kinetics of oligonucleotides obtained by coadministration with polyamine-cholesterol indicates that the oligonucleotides can be used at a lower effective dose in biological experiments. Thus, the new cationic compounds improved cellular uptake by up to 100 fold over controls, and uptake enhancement occurred in the presence of serum.

EXAMPLE 4

Stability of Oligonucleotides

Vero cells were incubated at 37° C. with 1 μM $^{35}$S-labeled oligonucleotide-3'-propylamine in the presence of spermidine-cholesterol at about a 1:2 mass ratio. At various time points, extracellular medium and cells were separated and the amount of total radioactivity in each sample was determined by scintillation counting. Intact oligonucleotides were then extracted from the medium and the cells by phenol-chloroform extraction and ethanol precipitation, and finally electrophoresed on 12% denaturing polyacrylamide gels. The amount of intact radiolabeled oligonucleotide was quantified. The figures show the amount of total radioactivity and intact radiolabeled oligonucleotide, plotted as a percentage of control oligonucleotide.

The integrity of oligonucleotides delivered into cells via the new uptake enhancers has been studied in Vero cells. End-protected oligonucleotides (containing 3'-propylamine; Zendegui et al., 1992) are known to be more stable than unmodified oligonucleotides (free 3'-OH) in the extracellular medium. There is a slight decrease in total radioactivity in the extracellular medium over 24 hours, presumably due to cellular uptake. Approximately 15% of the starting material is still intact after 24 hours. Loss of intact oligonucleotides appears to be due mostly to degradation as well as cellular uptake.

Figure 4A:
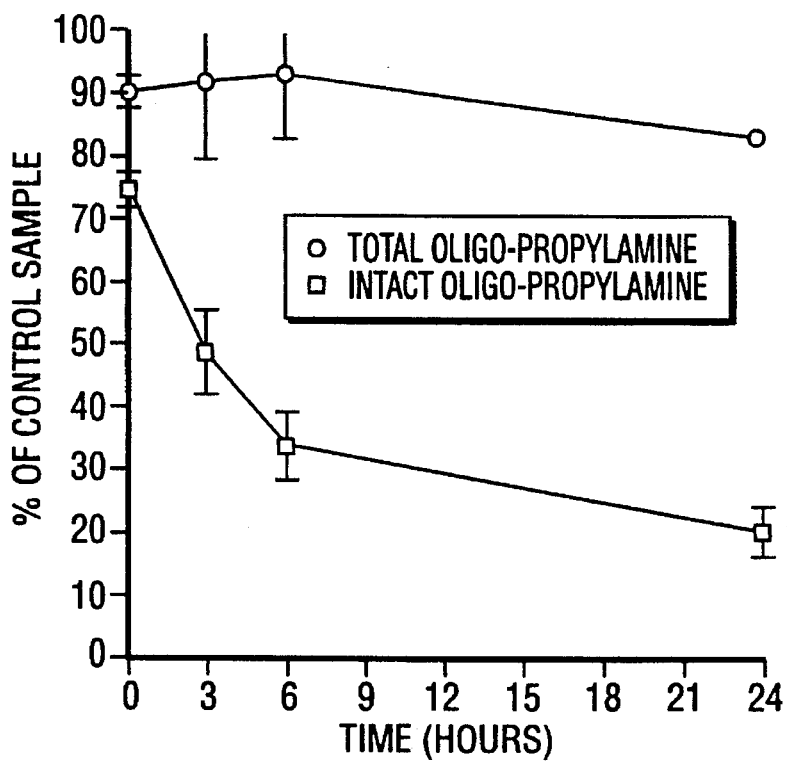
FIG. 4A–4B show the stability of oligonucleotides in the extracellular medium (FIG. 4A) and inside cells (FIG. 4B).
Figure 4B:
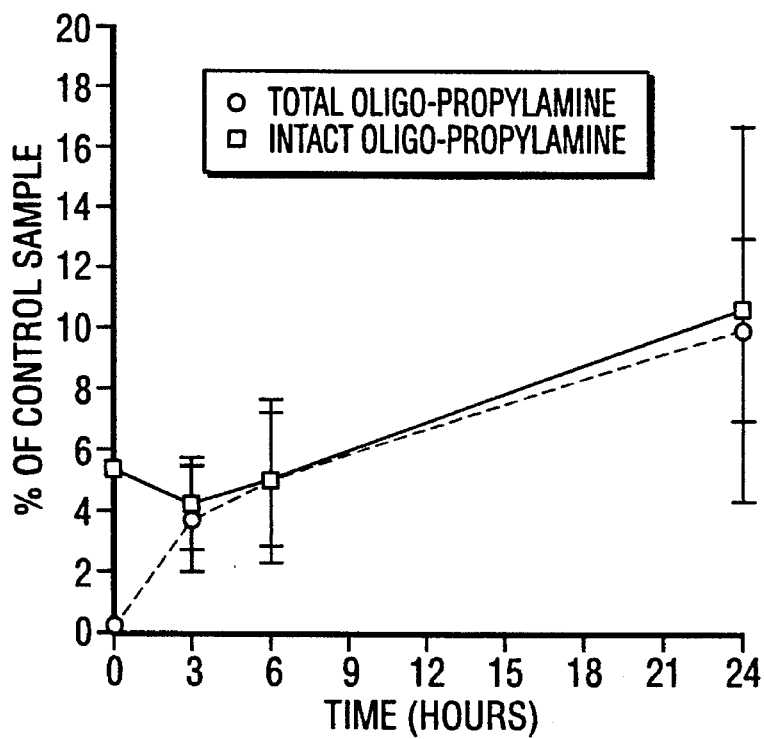

When Vero cells grown in medium containing 10% bovine serum were incubated with $^{35}$S-labeled oligomers, approximately 10% of the counts entered cells at the end of 24 hours (FIG. 4). Gel analysis indicated that approximately a third of oligonucleotides were still intact after 24 hours. More importantly, nearly all of the internalized material was also intact (FIG. 4).

These data suggest that the material inside cells is protected from endonuclease digestion.

The novel transporter of the present invention is more effective and versatile than the available compounds for improving the uptake of oligonucleotides by cells. Cells actively accumulate the oligonucleotides, and once inside, the oligonucleotides remain intact for longer periods of time. Transport into the nucleus is also facilitated. The uptake enhancers have utility in the delivery of any nucleic acid therapeutic that needs to enter cells, including but not limited to triple helix-forming oligonucleotides, antisense oligonucleotides, aptamers, and longer pieces of DNA for gene therapy.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The methods, procedures and treatments described herein are presently representative of preferred embodiments, are exemplary, and are not intended as limitations on the scope of the invention. Changes therein and other uses will occur to those skilled in the art which are encompassed within the spirit of the invention or defined by the scope of the appended claims.

What is claimed is:

1. An amphipathic transporter for delivery of nucleic acid into cells, comprising an essentially nontoxic, biodegradable cationic compound having a cationic head group capable of binding a nucleic acid and a lipid tail capable of associating with a cellular membrane, wherein said cationic head group is a polyamine, said lipid tail is cholesterol, and the cationic head group is linked to the lipid tail by a carbamate linkage.

2. The transporter of claim 1, wherein the polyamine is spermidine.

3. The transporter of claim 1, wherein the polyamine is spermine.

4. A compound comprising the transporter of claim 1, non-covalently bound to a nucleic acid.

5. The compound of claim 4, wherein the nucleic acid is selected from the group consisting of triplex forming oligonucleotides, antisense oligonucleotides, aptamers, ribozymes, plasmids and DNA.

6. A method of delivering nucleic acids into cells comprising the steps of:

forming a complex by non-covalently binding a nucleic acid to the transporter of claim 1, and contacting cells with the complex, whereby the nucleic acid is delivered into the cells.

7. A compound comprising an essentially non-toxic, biodegradable cationic compound having a cationic head group non-covalently bound to a nucleic acid and a hydrophobic group capable of associating with a cellular membrane;

said cationic head group being a polyamine;

said hydrophobic group being cholesterol; and said cationic head group being linked with said hydrophobic group by a carbamate linkage.

8. The compound of claim 7 wherein said polyamine is spermine and said nucleic acid is a triplex forming oligonucleotide.

9. The compound of claim 7 wherein said polyamine is spermidine and said nucleic acid is a triplex forming oligonucleotide.

* * * * *